United States Patent
Rajaiah et al.

(10) Patent No.: US 9,282,810 B2
(45) Date of Patent: Mar. 15, 2016

(54) ORAL CARE APPLICATOR

(75) Inventors: Jayanth Rajaiah, Loveland, OH (US); Connie Marie Roetker, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/289,180

(22) Filed: Nov. 4, 2011

(65) Prior Publication Data

US 2012/0118312 A1    May 17, 2012

Related U.S. Application Data

(60) Provisional application No. 61/410,577, filed on Nov. 5, 2010.

(51) Int. Cl.
| | |
|---|---|
| A61C 15/00 | (2006.01) |
| A46B 9/00 | (2006.01) |
| A61K 8/02 | (2006.01) |
| A61K 8/31 | (2006.01) |
| A61K 8/49 | (2006.01) |
| A61Q 11/00 | (2006.01) |

(52) U.S. Cl.
CPC . *A46B 9/005* (2013.01); *A61K 8/02* (2013.01); *A61K 8/31* (2013.01); *A61K 8/49* (2013.01); *A61Q 11/00* (2013.01)

(58) Field of Classification Search
CPC ........... A46B 9/005; A61K 8/02; A61K 8/49; A61K 8/31; A61Q 11/00
USPC ............... 132/320, 208, 309, 311; 15/104.93, 15/104.94, 244.1
See application file for complete search history.

(56) References Cited

U.S. PATENT DOCUMENTS

| | | | |
|---|---|---|---|
| 3,775,848 A * | 12/1973 | Barnett | 132/329 |
| 4,856,136 A | 8/1989 | Janssen et al. | |
| 4,887,994 A * | 12/1989 | Bedford | 604/1 |
| 4,918,103 A * | 4/1990 | Park et al. | 514/520 |
| 4,952,204 A | 8/1990 | Korteweg | |
| 5,130,122 A | 7/1992 | Tabibi et al. | |
| 5,310,563 A | 5/1994 | Curtis et al. | |
| 5,615,440 A * | 4/1997 | Cowan et al. | 15/104.94 |
| 5,944,519 A | 8/1999 | Griffiths | |
| 5,947,986 A | 9/1999 | Lewis | |
| 6,205,611 B1 * | 3/2001 | Vigil | 15/244.1 |
| 6,379,069 B1 | 4/2002 | May | |
| 6,383,475 B1 | 5/2002 | Meyers et al. | |
| 6,406,451 B1 | 6/2002 | Rowe | |
| 6,516,947 B1 | 2/2003 | Van Dyke et al. | |
| 6,517,350 B2 | 2/2003 | Diasti et al. | |
| 6,641,319 B2 | 11/2003 | May | |
| 6,660,776 B1 | 12/2003 | McDaniels, III | |
| 6,869,242 B2 | 3/2005 | May | |
| 7,044,671 B2 | 5/2006 | Parikh et al. | |
| 7,097,629 B2 | 8/2006 | Blair | |
| 7,201,527 B2 | 4/2007 | Thorpe et al. | |
| 7,309,185 B2 | 12/2007 | Thorpe et al. | |
| 7,597,497 B2 | 10/2009 | Levine | |

(Continued)

FOREIGN PATENT DOCUMENTS

| | | |
|---|---|---|
| WO | WO 2006/002957 | 1/2006 |
| WO | WO 2007/079069 | 7/2007 |

*Primary Examiner* — Rachel Steitz

(74) *Attorney, Agent, or Firm* — Alexandra S. Anoff

(57) ABSTRACT

Oral care applicators, including a tip, which can be optimized based on the desired use.

20 Claims, 3 Drawing Sheets

(56) References Cited

U.S. PATENT DOCUMENTS

| | | |
|---|---|---|
| 7,607,188 B2 | 10/2009 | Singhal |
| 7,887,788 B2 | 2/2011 | De La Poterie et al. |
| 2003/0003060 A1* | 1/2003 | McDaniels, III ............... 424/49 |
| 2003/0075200 A1* | 4/2003 | Gueret ........................ 132/320 |
| 2003/0091540 A1 | 5/2003 | Ahmad et al. |
| 2005/0196355 A1 | 9/2005 | Georgiades et al. |
| 2005/0281757 A1 | 12/2005 | Ibrahim et al. |
| 2006/0177384 A1* | 8/2006 | Brown ............................ 424/49 |
| 2006/0198799 A1 | 9/2006 | Giniger |
| 2006/0207627 A1 | 9/2006 | Thorpe et al. |
| 2006/0239757 A1 | 10/2006 | Giniger |
| 2006/0239938 A1 | 10/2006 | Perechocky |
| 2007/0020028 A1 | 1/2007 | Levine et al. |
| 2007/0037717 A1 | 2/2007 | Clark et al. |
| 2007/0048339 A1 | 3/2007 | Popplewell et al. |
| 2007/0183986 A1 | 8/2007 | Allred et al. |
| 2008/0023025 A1 | 1/2008 | Burtzlaff et al. |
| 2008/0112902 A1 | 5/2008 | Perechocky |
| 2008/0201884 A1 | 8/2008 | Vazquez et al. |

\* cited by examiner

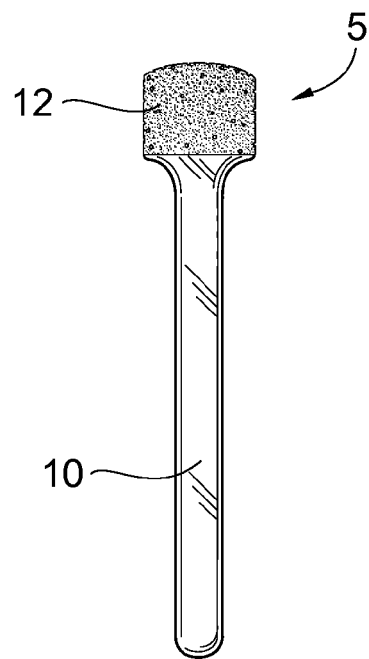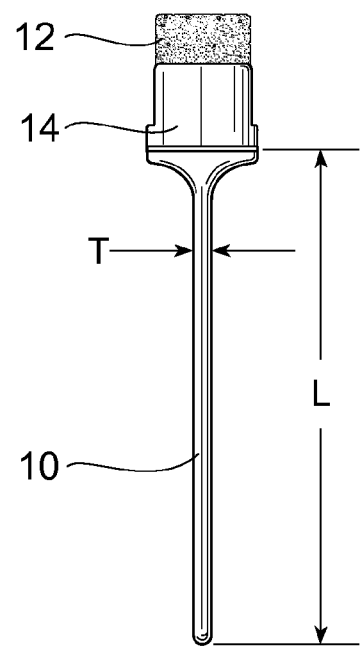
Fig. 1    Fig. 2
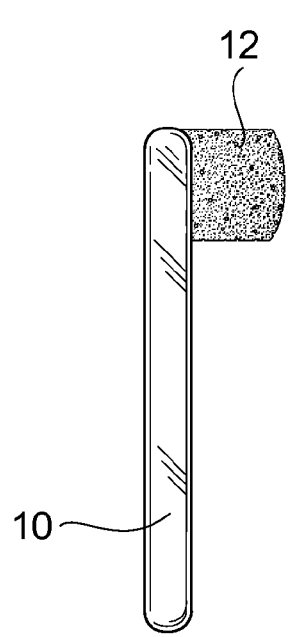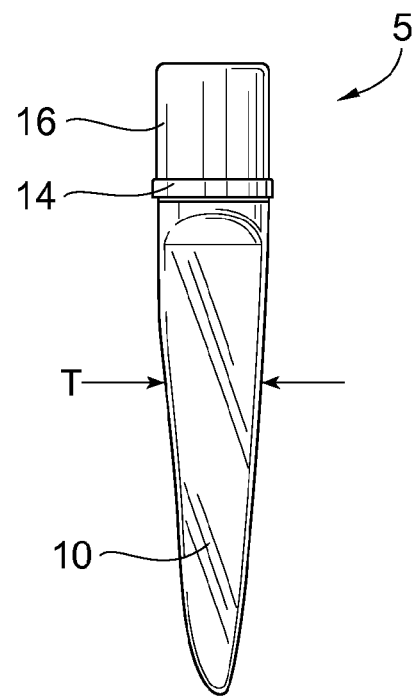
Fig. 3    Fig. 4

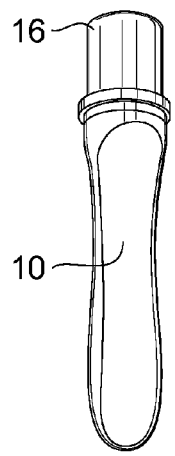 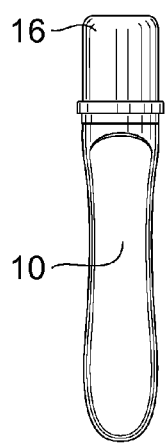 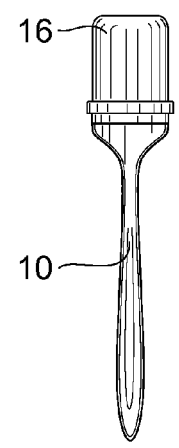 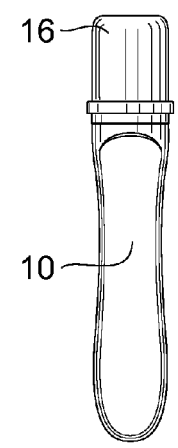 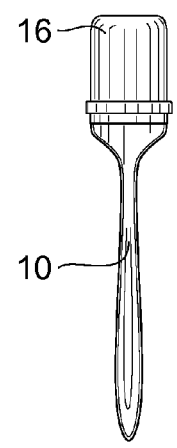
Fig. 5  Fig. 6  Fig. 7  Fig. 8  Fig. 9
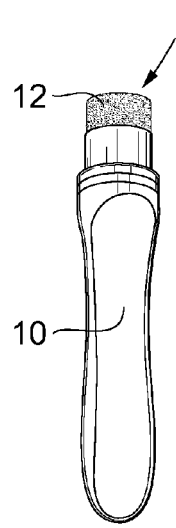 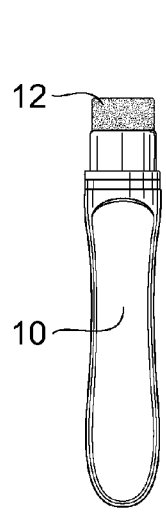 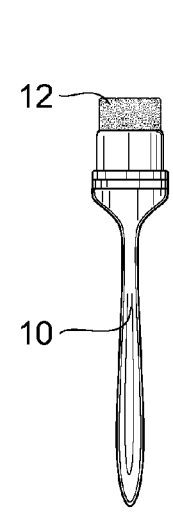 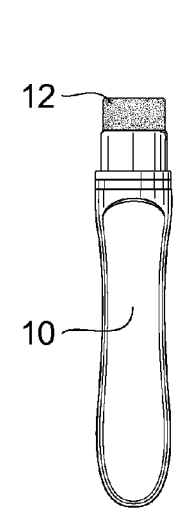 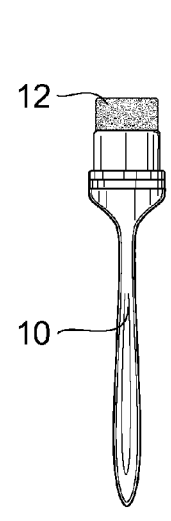
Fig. 10  Fig. 11  Fig. 12  Fig. 13  Fig. 14

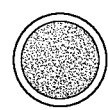  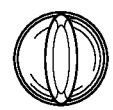
Fig. 15      Fig. 16
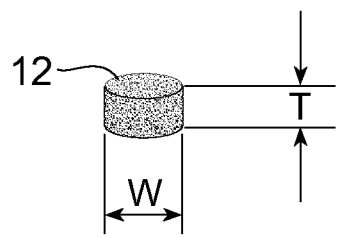
Fig. 17

ORAL CARE APPLICATOR

CROSS REFERENCE TO RELATED APPLICATION

This application claims the benefit of U.S. Provisional Application No. 61/410,577 filed on Nov. 5, 2010, which is incorporated herein by reference.

FIELD OF THE INVENTION

The subject matter of the application includes oral care applicators, compositions, and methods relating thereto.

BACKGROUND OF THE INVENTION

Consumers are constantly looking for ways to improve their oral hygiene. For most, this routine includes regular brushing. For others, this routine also includes floss, mouth wash, or other oral care agents. Many consumers find, however, the options for maintaining oral hygiene throughout the day are inconvenient or ineffective. For example, while it is recommended to brush after every meal, most consumers do not comply with this recommendation because routinely carrying a toothbrush is viewed as inconvenient or non-hygienic. Many times, consumers rely on products like gum or mints to give them that refreshed feeling between meals and brushings. These options, however, are often not totally satisfactory to the consumer. As such, there is a need for improved oral care applicators, kits, compositions, and methods relating thereto.

SUMMARY OF THE INVENTION

In one embodiment, the present invention is directed to an oral care kit, comprising: an applicator comprising; a handle, and a tip comprising a porous material with a compression load deflection from about 1.0 psi, wherein the tip is adjacent to the handle.

In another embodiment, the present invention is directed to an oral care applicator, comprising: a handle, wherein the handle has a width to thickness ratio of greater than or equal to 1.5; an open cell foam tip adjacent to the handle, wherein the foam tip has a compression load deflection from about 0.5 to about 2.0, and a water insoluble oral care composition is at least partially contained within the foam tip.

In an additional embodiment, the present invention is directed to a method of removing substances from teeth, comprising: contacting a tip of an applicator against at least a portion of a tooth, wherein the tip comprises a porous material having a compression load deflection from about 0.5 to about 2.0 and at least a portion of a substance is removed from the tooth.

These and other embodiments will be more readily apparent from the figures and description below.

BRIEF DESCRIPTION OF THE DRAWINGS

FIG. 1 is a front perspective view of an oral care applicator according to one embodiment of the invention;

FIG. 2 is a side view of an oral care applicator according to one embodiment of the invention;

FIG. 3 is a side perspective view of an oral care applicator according to one embodiment of the invention; and FIG. 4 is a front view of an oral care applicator according to one embodiment of the invention;

FIG. 5 is a perspective view of an oral care applicator according to one embodiment of the invention;

FIG. 6 is a front view of an oral care applicator according to one embodiment of the invention;

FIG. 7 is side view of an oral care applicator according to one embodiment of the invention;

FIG. 8 is a rear view of an oral care applicator according to one embodiment of the invention; and FIG. 9 is a side view of an oral care applicator according to one embodiment of the invention.

FIG. 10 is a perspective view of an oral care applicator according to one embodiment of the invention;

FIG. 11 is a front view of an oral care applicator according to one embodiment of the invention;

FIG. 12 is side view of an oral care applicator according to one embodiment of the invention;

FIG. 13 is a rear view of an oral care applicator according to one embodiment of the invention; and FIG. 14 is a side view of an oral care applicator according to one embodiment of the invention.

FIG. 15 is a top view of an oral care applicator according to one embodiment of the invention;

FIG. 16 is a bottom view of an oral care applicator according to one embodiment of the invention; and FIG. 17 is a perspective view of a portion of an oral care applicator according to one embodiment of the invention; and

DETAILED DESCRIPTION OF THE INVENTION

Consumers are always looking for products which will allow them the freedom to do what they want on-the-go. Oral hygiene is no exception. While many consumers do not utilize a toothbrush during the day due to feelings of sanitary concerns of traveling with a toothbrush or feelings of inconvenience, they often utilize mints or gum to help keep that freshly brushed feeling during the day. While mints and gum sometimes relieve feelings of bad breath, they often give only a short and limited benefit.

Additionally, even those consumers who choose to travel with and use a brush for cleanings during the day, brushing provides only a limited benefit due to its lack of proficiency in both cleaning the oral cavity and depositing an oral care composition in the oral cavity. For example, the oral care composition that is generally used with a brush is toothpaste. Tooth pastes are generally made to clean the teeth and the brush is designed to break-up the paste to form foam and to allow the spread of that foam and paste throughout the oral cavity. When you finish the brushing routine, there is little, if any, paste remaining in the oral cavity as the paste remnants are expectorated and often rinsed from the mouth. Any minute amount of paste remaining in the oral cavity after the brushing routine quickly dissipates into the saliva and is swallowed.

It has surprisingly been found that oral care applicators according to the present invention can provide both a cleaning benefit and deposition benefit. These benefits can be used for all areas of the oral cavity, for example, the teeth, tongue, gums, gingival margin, buccal lining, etc. For example, when an oral care composition is applied with an applicator according to the present invention, the tip will rub against the oral surface and remove things like biofilm, debris, etc. The tip will also start to compress either releasing the oral care composition when it is located within the tip or just spreading the oral care composition and depositing it, for example, on the teeth. Once the user has finished using the applicator, the deposited oral care composition remains behind on the teeth or other oral surfaces. The oral care composition will remain on the teeth or other oral surfaces until it is removed by mechanical action or washed away by saliva. Additionally, if the oral care composition is water insoluble, the residence time is believed to be longer due to the fact the composition is not solubilizing in the saliva. The composition can also provide for a hydrophobic layer on the teeth. This hydrophobic layer can make the teeth feel slick or smooth when contacted by the tongue of the user and to some users this slick free connotes a sense of clean teeth. Thus, the applicators give benefits which are not currently realized through brushing or the use of gum or mints.

Additionally, the applicators can be designed to be more easily transportable. For example, some embodiments of the applicators are generally smaller in size than a brush, can include the composition and applicator together, and/or can easily be designed for single usage. Thus, an applicator could be designed which has a reuseable handle with disposable tips or where the whole applicator is disposable after a single use. These types of embodiments also have the additional benefit of a further improved on-the-go type usage experience.

A more detailed discussion regarding the applicator and oral care compositions is below.

DEFINITIONS

As used herein, the terms "length", "thickness" (or "height"), and "width" describe the measurements of the handle and/or applicator herein and refer to relative dimensions. The length is typically the longest dimension, the width the next longest, and the thickness typically the shortest distance of the three. Guidance for measuring the handle may be seen in FIGS. 2 and 4, wherein "L" stands for length, "T" stands for thickness, and "W" stands for width. Similarly, guidance for measuring a tip with a circular cross-section is shown in FIG. 17.

However, one of ordinary skill would understand that in many instances, the thickness and width of the handle could be interchangeable or equivalent measurements. Furthermore, in certain handle or tip shapes where the cross section of the applicator is a curved figure (such as an oval), the width and/or thickness could be a diameter of the cross-section. In some embodiments of a handle with a circular cross-section, there may only be one measurement of thickness or width which is the diameter of the cross-section circle. In some embodiments of a tip with a circular cross-section, there may only be one measurement of width or length which is the diameter of the cross-section circle. Furthermore, in some embodiments, where the handle varies in dimensions over the length or width of the handle, the width could be the average width over the length and/or the thickness would be the average thickness over the length.

Applicator

The present application describes another on-the-go option for oral health. It is a convenient, easy to transport, oral care applicator. As can be seen in FIGS. 1, 2, and 10-16, in its basic form, the oral care applicator 5 comprises a handle 10 and a tip 12. The handle 10 can be made of any material suitable for use in or near the oral cavity. Some examples of materials suitable for use for the handle 10 include: polyethylene, polypropylene, acrylates, polymethyl methacrylates, metals, plastics, natural materials, synthetic materials, polyethylene teraphthalates, polybutylene teraphthalates, glass, and combinations thereof. In one embodiment, the handle comprises an acrylate. In another embodiment, the handle comprises a translucent plastic. In an additional embodiment, the handle comprises a clear plastic.

Additionally, the handle 10 can be of any size and shape that is suitable for application with the hand to the oral cavity. For example, in some embodiments, the handle length may be from about 20 mm to about 80 mm, from about 30 mm to about 70 mm, from about 30 mm to about 60 mm, from about 30 mm to about 50 mm, and/or, from about 35 mm to about 45 mm. In some embodiments the handle width may be from about 2 mm to about 15 mm, from about 3 mm to about 12 mm, from about 5 mm to about 10 mm, and/or about 7 mm to about 10 mm. Another parameter to consider when looking at the handle is the thickness. In one embodiment, the handle thickness may be from about 0.5 mm to about 5 mm, from about 0.7 mm to about 4 mm, from about 0.8 mm to about 3 mm, and/or, from about 1 mm to about 2.5 mm.

Another helpful parameter to consider for the handle is the external volume. The external volume of the handle does not include the volume of any voids in the handle. In some embodiments, the external volume of the handle is less than about 5 $cm^3$, less than about 4 $cm^3$, less than about 3 $cm^3$, less than about 2 $cm^3$, less than about 1.5 $cm^3$, and/or or less than about 1 $cm^3$.

Moreover, it has been discovered that particular combinations of these parameters yield a handle that is preferred by consumers. For example, one combination of parameters that can be used to help select a more consumer preferred handle is the width to thickness ratio. This ratio is calculated by dividing the width of the handle by the thickness of the handle. In some embodiments, the width to thickness ratio of the handle is from about 0.1 to about 20, from about 0.1 to about 10, from about 0.5 to about 5, from about 1 to about 4, from about 1.5 to about 3, and/or greater than about 1.5.

In one embodiment, the handle comprises an external volume of less than about 2 $cm^3$, a thickness less than about 0.5 cm, a width to thickness ratio from about 1 to about 4, a length from about 30 mm to about 50 mm, width from about 5 mm to about 10 mm, or a combination thereof.

In varying size parameters, the handle may likewise have any shape which is appropriate for use in the oral cavity. Some examples of shapes include flat, rounded, square, rectangular, beveled, curved, hour-glass-shaped, scallop-shaped, notched, serrated, chiseled, wavy, polygonal, and combinations thereof. The shape of the handle does not need to be uniform.

The other basic feature of an oral care applicator is the tip 12. The tip 12 can be any size which can be used in the oral cavity.

In some embodiments, the tip width is from about 0.2 cm to about 3.2 cm, from about 0.6 cm to about 2 cm, from about 0.6 cm to about 1.6 cm, and/or, from about 0.6 cm to about 1 cm.

In some embodiments, the tip length is from about 0.1 cm to about 3.2 cm, from about 0.2 cm to about 3.2 cm, from about 0.6 cm to about 2 cm, from about 0.6 cm to about 1.5 cm, and/or, from about 0.6 cm to about 1 cm.

In some embodiments, the tip thickness is from about 0.1 cm to about 1.6 cm, from about 0.3 cm to about 1 cm, from about 0.3 cm to about 0.8 cm, and/or, from about 0.3 cm to about 0.5 cm.

The external volume of the tip does not include any voids in the tip. In some embodiments, external volume of the tip is from about 0.05 $cm^3$ to about 1.6 $cm^3$ about 0.05 $cm^3$ to about 0.8 $cm^3$, from about 0.1 $cm^3$ to about 0.4 $cm^3$, from about 0.15 $cm^3$ to about 0.3 $cm^3$, from about 0.15 $cm^3$ to about 0.25 $cm^3$.

In some embodiments, the width over thickness ratio of the tip is from about 0.1 to about 20, from about 0.1 to about 10, from about 0.5 to about 5, from about 1 to about 4, from about 1.5 to about 3, and/or greater than about 1.5.

In one embodiment, the tip comprises an external volume of less than about 0.4 cm³, a thickness less than about 0.8 cm, a width to thickness ratio from about 1 to about 4, a length from about 0.6 cm to about 1 cm, a width from about 0.6 cm to about 1 cm, or a combination thereof.

Additionally, the shape may be any that can be used in the oral cavity, for example, round, square, octagonal, rectangular, hour-glass-shaped, scallop-shaped, notched, serrated, chiseled, wavy, polygonal, or a combination thereof. The top of the tip may likewise be flat, rounded, have apertures, on an angle, or a combination thereof. The tip 12 is generally located on top of the handle 10, like in FIG. 1, but could also be located on the side of the handle 10 as shown in FIG. 3.

The tip 12 can be made of any porous material suitable for use in the oral cavity. These materials include, for example, paper, foam, bundled fibers, and combinations thereof. One way of characterizing a porous material is through its density. This density is a measure of the tip's porosity. Porosity can affect the ability of the tip to dislodge and/or capture many residues within the oral cavity, like biofilm, plaque, food debris, stains, etc. Porosity can also affect the ability of the tip to contain an oral care substance within the tip. In one embodiment, the tip has a density from about 0.5 to about 8 lbs/ft³.

Another important feature of a porous material is its cellular structure. Porous materials can be open-celled and/or closed-celled. In one embodiment the tip is open-celled. In this embodiment, the open-celled structure allows for an oral care composition to at least partially reside within the tip, and, it also aides in capturing, holding, and/or dislodging many residues within the oral cavity, like biofilm, plaque, food debris, stains, etc. An open cell structure can also help in dispensing the oral care substance during use.

Another property of a porous material is the measure of its pores per square inch. This property is often perceived as the roughness of the material. In one embodiment, the tip has a pores per square inch of less than about 300.

An additional property to consider for the tip, one that can have a substantial effect on the consumer acceptance and uses for an applicator, is the compression load deflection (CLD). CLD is a measure of firmness or hardness and is expressed in Pounds Per Square Inch (PSI) at a given percentage deflection. CLD is measured by taking a sample, 2"×2"×1" thick. The sample is placed in an apparatus for measurement. The entire sample is typically compressed under a 50 in² circular indenter platen. The platen is driven into the foam sample stopping when it reaches a deflection depth of typically 0.25" (which is 25% of the initial 1 inch thickness). The testing device records the force in Pounds required to hold this indentation after one minute. The CLD, in PSI, is calculated by: [Pounds recorded]/[Cross-sectional area in square inches of the foam area to which the force is applied]. This CLD @25% (2"×2"×1") is typically reported in PSI. Other relevant methods, procedures, and apparatus are described in ISO 3386 and ASTM D-3574 which are incorporated herein by reference.

Compression load deflection is a measure of the hardness of the porous material. The less it condenses when compressed, the harder it is. When selecting the material for the applicator, it is important to consider both the desired application and consumer acceptability. For example, harder materials are generally more accepted in applications for cleaning teeth, but making it too hard will likely cause injury and/or irritation to the soft tissue leading to lower consumer acceptability. In the reverse, materials which are too soft for the desired application are often construed as too flimsy or may even fall apart. Consumers often identify materials that are too soft for the application based on a feel of flattening of the tip during use.

For some applications, like precisely cleaning hard surfaces like the teeth, a harder material is desired, while other applications, like cleaning soft gum tissue, lend themselves to a softer material. For those uses where application of a composition is desired, there also needs to be a balance between the hardness and softness of the material. It has to be soft enough to apply the composition, but not so soft that it applies all of the composition to one area. In one embodiment, the tip has a compression load deflection greater than about 1.0 psi. In another embodiment, the compression load deflection is from about 0.5 to about 2.5 psi. In varying embodiments, the compression load deflection is from about 0.5, 0.6, 0.7, 0.8, 0.9, 1.0, 1.2, 1.4, 1.6, 1.8, 2.0, to about 0.6, 0.7, 0.8, 0.9, 1.0, 1.2, 1.4, 1.6, 1.8, 2.0, 2.2, 2.4, 3.0, 3.5, 4.0, 5.0, 10.0 psi, or combinations thereof.

In one embodiment, the tip comprises foam. Foam can be either closed cell, open cell, or a combination thereof. In one embodiment, the tip comprises open cell foam. In a further embodiment, the open cell foam comprises polyurethane, polyethylene, silicone, or a combination thereof. One foam tip material which offers good flavor compatibility is polyurethane. In one embodiment the foam tip material comprises a an open cell polyether polyurethane foam with density ranging from about 2.00 to about 3.00 lbs/ft³, pore size ranging from about 65 to about 75 ppi, and/or CLD @ 25% (2"×2"×1") of at least about 1.00 psi. In one embodiment the foam tip material comprises EC250-70GA and/or EC250-70 GB from Foamtec International.

As shown in FIG. 4, the oral care applicator 5 can also include a collar 14. The collar can serve as a platform on which to place the tip. It can also serve as a barrier between any oral care composition in and/or on the tip 12 and the handle 10, so that when pressure is applied to the tip during application of the oral care composition, the composition cannot squeeze out of the bottom of the foam and run down the handle. In some embodiments, the collar can also make it easier to manufacture the applicator parts.

Also shown on FIGS. 4 and 5-9, is a cap 16. A cap can act as a barrier to contamination of the tip 12 before it is used. It can also prevent any oral care composition in the tip 12 from drying out due to air exposure, loss of volatiles, loss of flavors or scents, etc. A cap 16 also allows the oral care applicator to be more easily portable as it can more easily be carried in a purse or pocket.

The oral care applicator can also be contained within a case. The case may contain one or more applicators and can be used, for example, for ease of portability or a place to store before and/or after use.

Oral Care Composition

Depending on the intended use of the applicator, it can be used in combination with an oral care composition. The oral care composition can be anything desired for use in the oral cavity. For example, it can range from merely a prophylactic use to delivery of actives. The oral care composition may be separate from the applicator, contained in a reservoir either in or on the oral care applicator, contained on, around, or within the tip, or some combination thereof. For example, in one embodiment, the oral care composition is pre-impregnated within an open cell foam tip. When the oral care composition is pre-impregnated into the foam tip, the majority of the composition will be contained within the voids created by the open cell nature of the foam. Some of the composition, however, may reside on the exterior of the foam, like on the sides or top.

The oral care composition can include many components, for example, a carrier, sweetener, flavor, sensate, other additives, etc. Various combinations of the components are possible and are considered within the scope of the invention, a few specific combinations are discussed below.

Additionally, the oral care composition may be water soluble or water insoluble. The term "water-insoluble" as used herein refers to a material that is less than about 10% soluble in water, unless specifically stated otherwise. Additional disclosure regarding water insoluble oral care compositions useful herein can be found in U.S. patent application Ser. No. 12/857,620, published as Publication 2011/0038810 A1 on Feb. 17, 2011 and assigned to the Procter & Gamble Company.

In one embodiment, the oral care composition is water insoluble. In a further embodiment, the water insoluble oral care composition comprises a water insoluble carrier. In another embodiment, an oral care composition comprises a water insoluble carrier, a sweetener, and an additional component selected from a sensate, a flavor, or combination thereof. In another embodiment, an oral care composition consists essentially of a water insoluble carrier, a sweetener, and an additional component selected from a sensate, a flavor, or a combination thereof.

In a further embodiment, the oral care composition comprises at least 75% by weight of the water insoluble carrier. In another embodiment, the water insoluble carrier is from about 70% to about 99% by weight of the oral care composition. In an additional embodiment, the water insoluble carrier is from about 50% to about 99% by weight of the oral care composition.

In another embodiment, the water insoluble carrier is selected from the group consisting of: rubber, natural wax, synthetic wax, polyvinyl chloride, nylon, fluorocarbon, polyurethane prepolymer, polyethylene, polystyrene, polypropylene, petrolatum, polyvinyl acetate, natural oil, synthetic oil, fats, silicone, hydrocarbons, caprilic/capric triglycerides, oleic acid, stearic acid, and mixtures thereof. In one embodiment, the water insoluble carrier comprises microcrystalline wax, paraffin wax, bees wax, petrolatum, mineral oil, polybutene, silicone, natural oil, synthetic oil, polyethylene, or combinations thereof. In a further embodiment, the water insoluble carrier is selected from the group consisting of polybutene, silicones, petrolatum, and combinations thereof. In another embodiment, the carrier comprises petrolatum. In yet another embodiment, the carrier consists essentially of petrolatum.

In a further embodiment, the oral care composition comprises from about 0.5% to about 10% by weight of a sweetener. In one embodiment, the sweetener is selected from a group consisting of dextrose, fructose, corn syrup, high fructose corn syrup, aspartame, saccharin, sugar alcohols, and mixtures thereof. In a one embodiment, the sweetener is selected from the group consisting of saccharin, sucralose, Rebiana, xylitol, aspartame, Acesulfame K, mono ammoniated glycyrrhizinate, and mixtures thereof. In another embodiment, the sweetener comprises saccharin, sucralose, Rebiana, or a combination thereof.

In another embodiment, the sum of the weight percentages of the sweetener and the additional component is less about 25%. In another embodiment the sum of the weight percentages of the sweetener and the additional component is less than 25%. In an additional embodiment, the sum of the weight percentages of the sweetener and the additional component is from about 8% to about 15%.

In one embodiment, the additional component comprises a flavor. In a further embodiment, the flavor is selected from the group consisting of: peppermint, spearmint, vanilla, cinnamon, wintergreen, mint, strawberry, grape, apple, and combinations thereof. In a further embodiment, the flavor component comprises mixed mint, peppermint, spearmint, wintergreen, or a combination thereof. In an additional embodiment, the flavor component consists essentially of mint. In one embodiment, the ratio of flavor to sweetener ("R2") is from about 0.2 to about 20.

In one embodiment, the additional component comprises a sensate. In one embodiment, the sensate comprises a coolant. In another embodiment, the sensate is selected from the group consisting of menthol, menthyl lactate, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, thymol, linalool, benzaldehyde, cinnamaldehyde glycerol acetal, and mixtures thereof. In another embodiment, the sensate is selected from the group consisting of menthol; 3-1-menthoxypropane-1,2-diol; methyl lactate; N,2,3-trimethyl-2-isopropylbutanamide; N-ethyl-p-menthan-3-carboxamide; N-(4-cyanomethylphenyl)-p-menthanecarboxamide, and combinations thereof. In a further embodiment, the sensate comprises menthol; N,2,3-trimethyl-2-isopropylbutanamide; N-(4-cyanomethylphenyl)-p-menthanecarboxamide; or a combination thereof. In an additional embodiment, the ratio of sensate to sweetener ("R3") is from about 0.2 to about 20.

In another embodiment, the additional component comprises a combination of flavor and sensate. In one embodiment, the ratio by weight of flavor plus sensate to sweetener ("R4") is from about 0.4 to about 40. In another embodiment, the ratio by weight of sensate to flavor ("R1") is from about 0.5 to about 2.0, the ratio by weight of flavor to sweetener is from about 1.0 to about 4.0, the ratio by weight of sensate to sweetener is from about 1.0 to about 4.0, and the ratio by weight of flavor plus sensate to sweetener is from about 2.0 to about 8.0. In an additional embodiment, the oral care composition comprises from about 1% to about 10% by weight of flavor and from about 1% to about 10% by weight of sensate.

In one specific embodiment, the oral care composition consists essentially of a water insoluble carrier, a sweetener, and an additional component selected from the group consisting of sensate, flavor, and combinations thereof, wherein the composition is configured for application within the oral cavity. In another specific embodiment, an oral care composition consists essentially of petrolatum, saccharin, mint oil, and menthol and is configured for application to the teeth. In a further embodiment, the ratio by weight of flavor plus sensate to sweetener is from about 0.4 to about 40. In another embodiment, the ratio by weight of sensate to flavor is from about 0.5 to about 2.0, the ratio by weight of flavor to sweetener is from about 1.0 to about 4.0, the ratio by weight of sensate to sweetener is from about 1.0 to about 4.0, and the ratio by weight of flavor plus sensate to sweetener is from about 2.0 to about 8.0. In another embodiment, the ratio by weight of flavor plus sensate to sweetener is from about 0.4 to about 40. In another embodiment, the ratio by weight of sensate to flavor is about 1.0, the ratio by weight of flavor to sweetener is about 2.0, the ratio by weight of sensate to sweetener is about 2.0, and the ratio by weight of flavor plus sensate to sweetener is about 4.0.

In addition to those components listed above, the oral care composition may additionally include other components. One example of these additional components includes substantivity agents. One group of substantivity agents is organophosphates. Suitable organophosphate compounds have a strong affinity for the tooth surface and have sufficient surface binding propensity to desorb pellicle proteins and remain affixed thereon. The phosphate groups of the organophosphate attach themselves to cations, in particular calcium ions in teeth or some other positively charged sites such as protein residues on the mucosal surface and thus serve to anchor the hydrophobic portion of the molecule onto the surface thereby modifying it to be hydrophobic. The phosphate groups provide ready bonding/binding to cationic and charged surfaces via electrostatic interaction, hydrogen bonding, or complexation, which leads to ready deposition of the organophosphate upon application to form a coating on the treated surface. The strong bond results in longer retention or durability and substantivity of the coating.

Examples of suitable organophosphate compounds are mono-, di- or triesters represented by the following general structure wherein $Z^1$, $Z^2$, or $Z^3$ may be identical or different, at least one being an organic moiety, preferably selected from linear or branched, alkyl or alkenyl group of from 6 to 22 carbon atoms, optionally substituted by one or more phosphate groups; alkoxylated alkyl group or alkoxylated alkenyl group.

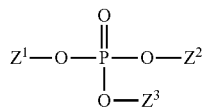

Some preferred agents include alkoxylated alkyl or alkenyl phosphate esters represented by the following structure:

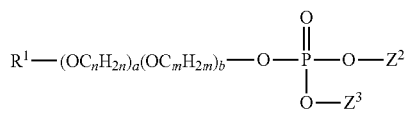

wherein $R^1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; $Z^2$ and $Z^3$ may be identical or different, each represents hydrogen, alkali metal, ammonium, protonated alkyl amine or protonated functional alkyl amine such as an alkanolamine, or a $R^1$—$(OC_nH_{2n})_a(OC_mH_{2m})_b$— group. Preferably, $R^1$ is an alkyl group of at least 10 carbon atoms and a and b are each no more than 10 in order to maintain overall hydrophobic character of the organophosphate and the degree of hydrophobicity imparted to the surface.

In one embodiment, the substantivity agent includes mono- di- and tri-alkyl and alkyl (poly)alkoxy phosphates such as dodecyl phosphate, lauryl phosphate; laureth-1 phosphate; laureth-3 phosphate; laureth-9 phosphate; dilaureth-10 phosphate; trilaureth-4 phosphate; $C_{12-18}$ PEG-9 phosphate and salts thereof. Many are commercially available from suppliers including Croda; Rhodia; Nikkol Chemical; Sunjin; Alzo; Huntsman Chemical; Clariant and Cognis. In one embodiment, the substantivity agent comprises monoalkyl phosphate.

Another example of an additional component includes actives. Some examples of actives include various fluoride salts for caries prevention and remineralization; gingivitis prevention by the use of antimicrobial agents such as triclosan, cetylpyridinium chloride, stannous fluoride, zinc citrate or essential oils; and hypersensitivity control through the use of ingredients such as strontium chloride, stannous fluoride, or potassium nitrate; pyrophosphate salts can be used as antitartar agents; peroxides can be used for bleaching and antiseptics; and polymeric mineral surface active agents such as phosphorylated polymers, in particular polyphosphates that bind to teeth, or metal ions such as stannous, zinc or copper that form insoluble compounds that deposit onto teeth, can be used for erosion protection or sensitivity protection. These actives can be used alone or in combination.

Another example of an additional component includes adhesive components. The present invention may comprise a safe and effective amount of an adhesive component, generally at a level of from about 1% to about 75% by weight of the composition. In other embodiments, the adhesive component is in the range of from about 1%, 5%, 10%, 15%, 20%, 25%, 30%, 35%, 40% to about 10%, 15%, 20%, 50%, 60%, 75%, or any combination thereof. In one particular embodiment, the adhesive component is in an amount from about 10.0% to about 60.0%. In another embodiment, the adhesive component is in an amount from about 1% to about 15%.

In general, adhesive components are hydrophilic particles that become sticky when activated by moisture or are hydrophilic liquids. For those that activate with moisture, moisture can be present, for example, in the oral care composition itself as well as in the oral cavity of the user. In varying embodiments, the adhesive components herein are mucoadhesive, adhesive to the teeth, hydrophilic, water soluble, have the property of swelling upon exposure to moisture, or any combination thereof.

In one embodiment the adhesive component is selected from the group consisting of: glycerin, polyoxamer, sorbitol, polyox, carbomer, polyacrylamides, polypeptides, natural gums; synthetic polymeric gums; AVE/MA; AVE/MA/IB; copolymers of maleic acid or anhydride and ethylene, styrene, and/or isobutylene, polyacrylic acid and/or polyacrylates thereof; polyitaconic acid, mucoadhesive polymers; water-soluble hydrophilic colloids; saccharide; cellulose; cellulosic resin, acrylic resin, their derivatives, and mixtures thereof. Examples of such materials include karaya gum; guar gum; gelatin; algin; sodium alginate; tragacanth; chitosan; acrylamide polymers; carboxypolymethylene; polyvinyl alcohol; polyamines; polyquarternary compounds; polyvinylpyrrolidone or its copolymers; cationic polyacrylamide polymers; salts and mixed salts of AVE/MA; polymeric acids, polymeric salts, and copolymers thereof; polyitaconic acid salts; polyhydroxy compounds; their derivatives; and mixtures thereof.

In another embodiment, the adhesive component is selected from the group consisting of: cellulose, cellulose derivatives (such as methylcellulose, carboxymethylcellulose, hydroxyethylcellulose, hydroxypropylcellulose, hydroxy-propylmethylcellulose, corn starch, and mixtures thereof), starch, starch derivatives, saccharide, saccharide derivatives, polyethylene oxides, polyethylene glycols, polyvinyl alcohols, carrageenan, alginates, karaya gums, xanthan gums, guar gums, gelatins, algins, tragacanth, chitosan, acrylamide polymers, carboxypolymethylenes, polyamines, poly quaternary compounds, polyvinylpyrrolidone, AVE/MA, salts of AVE/MA, mixed salts of AVE/MA, polymeric acids, polymeric salts, polyhydroxy compounds, and mixtures thereof.

In one embodiment the composition is substantially free of surfactants, abrasives, fluoride sources, therapeutic actives, muco-adhesives, polybutenes, silicones, and/or antimicrobial agents. In one embodiment, the oral care composition is not a dentifrice. In another embodiment, the oral care composition is not a rinse. In another embodiment, the oral care composition is not a denture adhesive.

Combinations

Described below are some specific combinations of applicator and oral care components. These should be understood as exemplary embodiments of the invention, but the invention is in no way limited to only these embodiments.

In one embodiment, an oral care applicator comprises a handle and a porous tip, wherein the tip is located on an end of the handle and comprises a CLD of from about 0.5 to about 2.0, and a water insoluble oral care composition is contained at least partially within the foam tip.

In one embodiment, an oral care applicator comprises a handle and a foam tip, wherein the foam tip is located on an end of the handle and comprises a CLD of from about 0.5 to about 2.0, and a water insoluble oral care composition is contained at least partially within the foam tip.

In another embodiment, an oral care applicator comprises a handle, a collar located on an end of the handle, and an open cell foam tip located adjacent to the collar, wherein a water insoluble oral care composition is at least partially contained within the tip, the tip has a CLD of greater than about 0.5 and a density of about 0.5 to about 8.0 lbs/ft$^3$.

In an additional embodiment, the oral care applicator comprises a handle, an open cell polyurethane foam tip, and a water insoluble oral care composition comprising petrolatum, wherein the oral care composition is contained at least partially within the tip and the tip has a CLD of from about 1.1 to about 2.0.

Methods of Use

The oral care applicator as discussed herein can be used in many ways. For example, the applicator itself may be used to remove biofilm from the teeth. Biofilm is a very thin layer on the surfaces of the oral cavity, like the teeth, that is often is made up of microorganisms. Biofilm is often recognized by consumers by the feel of it when they pass their tongue over their teeth. Biofilm can also develop into a thicker layer and at that stage is often referred to as plaque. Biofilm is also generally sticky and can contribute to food particles sticking to the teeth. By contacting the tip of an applicator to the tooth surface, the biofilm is interrupted and at least part of the biofilm is removed from the teeth and deposited on the tip, inside the tip, or a combination thereof. The removed biofilm can be visible on a lightly colored tip and can be used as a signal to consumers of the cleaning effect of the applicator.

The applicator can also be used to deliver an oral care composition. The oral care composition can be used to treat many conditions of the oral cavity. These conditions can include, for example, tooth sensitivity, gingivitis, stains, plaque, tartar, erosion, etc. Treatment can be effected based on the application of the oral care composition, an oral care active, or a combination thereof. Examples of such oral care actives include stannous sources, fluoride sources, peroxide sources, bleach sources, anti-microbial sources, etc.

In one embodiment, the application of the composition can treat tooth sensitivity. The applicator can, for example, treat for sensitivity by depositing a generally uniform layer of the oral care composition on the oral surface to be treated. This can be used for treatment of the whole oral cavity or spot treatment of a specific area, like a target tooth, within the oral cavity. For water insoluble oral care compositions, it is believed the delivery by the inventive applicators can block the tubules leading to reduced sensitivity by the formation of a layer over the entrance of the tubules. Additionally, in some instances, the applicator can also push substances into the tubules providing a further benefit through occlusion. In addition to the occlusion mechanism, a further sensitivity benefit can be achieved through the delivery of sensitivity agents as part of the oral care composition. Sensitivity agents can work, for example, by helping to further block tubules based on inherent particle size, particle size reduction through the application mechanism, or particle generation or size increase through mechanisms like precipitation, and even other agents work by acting on the nerves themselves to reduce their sensitivity to stimuli like hot or cold. Some examples of sensitivity agents include, for example, potassium salts, like potassium nitrate, potassium bicarbonate, potassium chloride, and potassium oxalate; strontium salts; lithium nitrate; sodium nitrate; hydroxylapatite fluoroapatite; ammonium oxalate; EDTA with fluoride; fluoride; ammonium glycyrrhizinate, etc.

The applicator can also be used to treat oral conditions that are found in or near crevices in the oral cavity, especially between teeth or at the gingival margin, for example. Examples of such oral conditions include gum-disease, staining, plaque, tartar, etc. In one embodiment, the applicator is designed for application of an oral care composition for all areas of the teeth and gums. In a further embodiment, this applicator is designed so the oral care composition can be delivered to the crevice by the tip. In one embodiment, the tip is at an angle allowing for better application to crevices and between teeth. It is believed this is a benefit which would not be found by using a conventional brush as bristles are designed to remove substances from crevices not deposit them.

EXAMPLES

Example 1

Comparison of CLD

Three applicators are assembled and tested to determine if there is consumer preference for a foam tip with a particular compression load deflection value. Applicators A-C are assembled by using a Loctite medical grade adhesive to secure 8 mm diameter by 4 mm in thickness disks of open celled polyurethane foam tips (with varying CLD) to the end of a 8 mm in diameter by 50 mm long acrylic handle. The CLD for the applicators is as follows: A (1.80), B (1.19), and C (0.61). The foam tips are then impregnated with 0.1 g of an oral care composition. The applicators are then paired A/B and B/C. The pairs of applicators are given to consumers who choose their preference from each pair.

In the A vs. B pairing, consumers prefer A over B at a rate of 4:1. In the B vs. C pairing, consumers prefer B over C at a rate of 5:0. Consumer questionnaires show A is preferred over B due to perceived differences in cleanability and composition delivery. Since A has a higher CLD, it is generally harder than B and likely led to consumers' impression it would be better able to clean the teeth and would give better composition delivery. Similar results are seen in the B versus C pairing, except there is a more overwhelming preference for B over C. Without being limited by theory, it is believed this is due to the CLD of C being close to that which consumers would start to find unacceptable for an applicator being used for application of an oral care composition to the oral cavity.

Example 2

Various Compositions of the Invention

The following non-limiting examples further illustrate and describe the embodiments of the subject invention wherein both essential and optional ingredients are combined. It is to be understood that the examples are given solely for the purpose of illustration and are not to be construed as limiting the scope of the present invention, as many variations thereof are possible without departing from the spirit and scope of the invention.

| Microcrystalline | A % | B % | C % | D % | E % | F % | G % | H % | I % | J % | K % |
|---|---|---|---|---|---|---|---|---|---|---|---|
| Wax W835 | 0 | 48 | 0 | 0 | 48 | 0 | 0 | 0 | 10 | 10 | 0 |
| Mineral Oil | 0 | 42 | 0 | 0 | 34 | 0 | 0 | 0 | 0 | 0 | 0 |
| Petrolatum | 90 | 0 | 0 | 82 | 0 | 90 | 89 | 88 | 80 | 79 | 94 |
| Mixed Mint Flavor | 4 | 4 | 4 | 8 | 8 | 8 | 2 | 4 | 4 | 4 | 4 |
| Menthol | 4 | 4 | 4 | 8 | 8 | 1 | 8 | 4 | 4 | 4 | 0 |
| Saccharin (Powder) | 2 | 2 | 2 | 2 | 2 | 1 | 1 | 4 | 2 | 2 | 2 |
| Versagel 750 M (or 1600 M) | 0 | 0 | 90 | 0 | 0 | 0 | 0 | 0 | 0 | 1 | 0 |
| | 100.0 | 100.0 | 100.0 | 100.0 | 100.0 | 100.0 | 100.0 | 100.0 | 100.0 | 100.0 | 100.0 |
| R1 | 1.00 | 1.00 | 1.00 | 1.00 | 1.00 | 0.13 | 4.00 | 1.00 | 1.00 | 1.00 | 0.00 |
| R2 | 2.00 | 2.00 | 2.00 | 4.00 | 4.00 | 8.00 | 2.00 | 1.00 | 2.00 | 2.00 | 2.00 |
| R3 | 2.00 | 2.00 | 2.00 | 4.00 | 4.00 | 1.00 | 8.00 | 1.00 | 2.00 | 2.00 | 0.00 |
| R4 | 4.00 | 4.00 | 4.00 | 8.00 | 8.00 | 9.00 | 10.00 | 2.00 | 4.00 | 4.00 | 2.00 |

To make the above example compositions B, E, I, and J the wax is melted at 95° C. and the other components are mixed into it at the elevated temperature. To make the above examples A, C, D, F, G, H, and K the petrolatum and/or Versagel is heated to about 70° C. and the other components are mixed in at the elevated temperature. For all examples, the compositions are allowed to come to room temperature prior to use.

Furthermore, each of the above example formulations may also be mixed with each other to provide hybrid-examples.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care applicator comprising:
   a. a handle comprising an end and a width from about 2 mm to about 15 mm wherein the handle is unitary;
   b. a foam tip located on top of the handle comprising a length from about 0.1 cm to about 2 cm and a compression load deflection greater than about 1.0 psi wherein a top of the tip is flat and wherein the tip is adapted to remove biofilm from a user's teeth;
   c. a water insoluble oral care composition comprising a water insoluble carrier selected from the group consisting of petrolatum, mineral oil, polybutene, silicone, polyethylene, or combinations thereof; wherein the oral care composition is associated with the foam tip.

2. The oral care applicator of claim 1 wherein the compression load deflection is greater than about 1.4 psi.

3. The oral care applicator of claim 1 further comprising a collar.

4. The oral care applicator of claim 1 wherein the foam tip is attached the end of the handle by an adhesive.

5. The oral care applicator of claim 1 wherein the oral care composition is at least partially contained within the tip.

6. The oral care applicator of claim 1 wherein the foam tip comprises an open cell foam.

7. The oral care applicator of claim 6 wherein the open cell foam comprises less than about 300 pores per square inch.

8. The oral care applicator of claim 6 wherein the open cell foam comprises a density of from about 0.5. to about 8.0 lbs/ft$^3$.

9. The oral care applicator of claim 1 wherein the oral care composition provides an anti-stain benefit.

10. The oral care applicator of claim 1 wherein the oral care applicator and the oral care composition are adapted to remove biofilm on a user's teeth.

11. The oral care applicator of claim 1 wherein the oral care composition is adapted to remain behind on a user's teeth after use.

12. The oral care applicator of claim 11 wherein the water insoluble carrier comprises petrolatum.

13. The oral care applicator of claim 12 wherein the oral care composition is released when the foam tip is compressed.

14. The oral care applicator of claim 11 wherein the oral care composition is at least partially contained within the foam tip.

15. The oral care applicator of claim 11 wherein the handle comprises a width from about 2 mm to about 15 mm and wherein the handle is unitary.

16. The oral care applicator of claim 11 wherein the foam tip comprises a length from about 0.1 cm to about 2 cm.

17. The oral care applicator of claim 11 wherein the foam tip comprises an open cell foam wherein the open cell foam has a density of from about 0.5 to about 8.0 lbs/ft$^3$.

18. The oral care applicator of claim 1 wherein the oral care composition is adapted to deposit a hydrophobic layer on the teeth that feels slick or smooth when contacted by a tongue of a user.

19. An oral care applicator comprising:
   a. a handle;
   b. a foam tip comprising a compression load deflection greater than about 1.0 psi wherein the tip is adapted to remove biofilm from a user's teeth; and
   c. a water insoluble oral care composition comprising a flavor, a sweetener selected from the group consisting of dextrose, fructose, corn syrup, high fructose corn syrup, aspartame, saccharin, sugar alcohols, and combinations thereof; and at least about 75% by weight of a water insoluble carrier selected from the group consisting of petrolatum, mineral oil, polybutene, silicone, polyethylene, or combinations thereof wherein the oral care composition is associated with the foam tip; and
   d. a cap wherein the cap is a single unit and wherein the cap prevents loss of the flavor.

20. The oral care applicator of claim 19 wherein a cross section of the foam tip is cylindrical and wherein a cross section of the cap is cylindrical.

\* \* \* \* \*